United States Patent [19]

Tozawa et al.

[11] Patent Number: 5,298,642
[45] Date of Patent: Mar. 29, 1994

[54] PROCESS OF OPTICALLY RESOLUTING OPTICALLY ACTIVE PLATINUM COMPLEX COMPOUND

[75] Inventors: Takeshi Tozawa; Yasunobu Komoda; Junji Ohnishi; Yukie Masuda; Junichi Taniuchi; Chihiro Nakanishi; Koji Okamoto, all of Kanagawa, Japan

[73] Assignee: Tanaka Kikinzoku Kogyo K.K., Japan

[21] Appl. No.: 43,577

[22] Filed: Apr. 7, 1993

[30] Foreign Application Priority Data

Apr. 22, 1992 [JP] Japan .................................. 4-129668

[51] Int. Cl.$^5$ ............................................. C07F 15/00
[52] U.S. Cl. .................................................... 556/137
[58] Field of Search ........................................ 556/137

[56] References Cited

U.S. PATENT DOCUMENTS

| | | | |
|---|---|---|---|
| 4,255,347 | 3/1981 | Kidani et al. | 260/429 R |
| 4,864,043 | 9/1989 | Nowatari et al. | 556/40 |
| 4,921,984 | 5/1990 | Nowatari et al. | 556/40 |
| 5,068,376 | 11/1991 | Nowatari et al. | 556/137 |
| 5,128,493 | 7/1992 | Nowatari et al. | 556/137 |

FOREIGN PATENT DOCUMENTS 0041644 12/1981 European Pat. Off. ............ 556/137
0275559 7/1988 European Pat. Off. ............ 556/137

Primary Examiner—Jose' G. Dees
Assistant Examiner—Perfirio Nazario-Gonzalez
Attorney, Agent, or Firm—Klauber & Jackson

[57] ABSTRACT

Disclosed herein is a process of optically resoluting optically active platinum complex compounds which comprises optically resoluting a d-isomer and an l-isomer of a cis-Pt(II) complex of a 1,2-cyclohexanediamine isomer characterized in that the mixture of the d-isomer and the l-isomer is optically resoluted by means of high performance liquid chromatography employing a column packed with a chiral filler.

The chiral filler include, for example, a cellulose ester derivative, a cellulose carbamate derivative, an amylose carbamate derivative, a polymethacryl acid ester and $\beta$- and $\gamma$-cyclodextrin.

According to the present invention, the optical resolution of a platinum complex compound essentially consisting of the mixture of two optical isomers which cannot be resoluted in accordance with a normal resolution method due to the small structural difference can be easily performed utilizing the characteristics of a chiral filler.

2 Claims, 1 Drawing Sheet

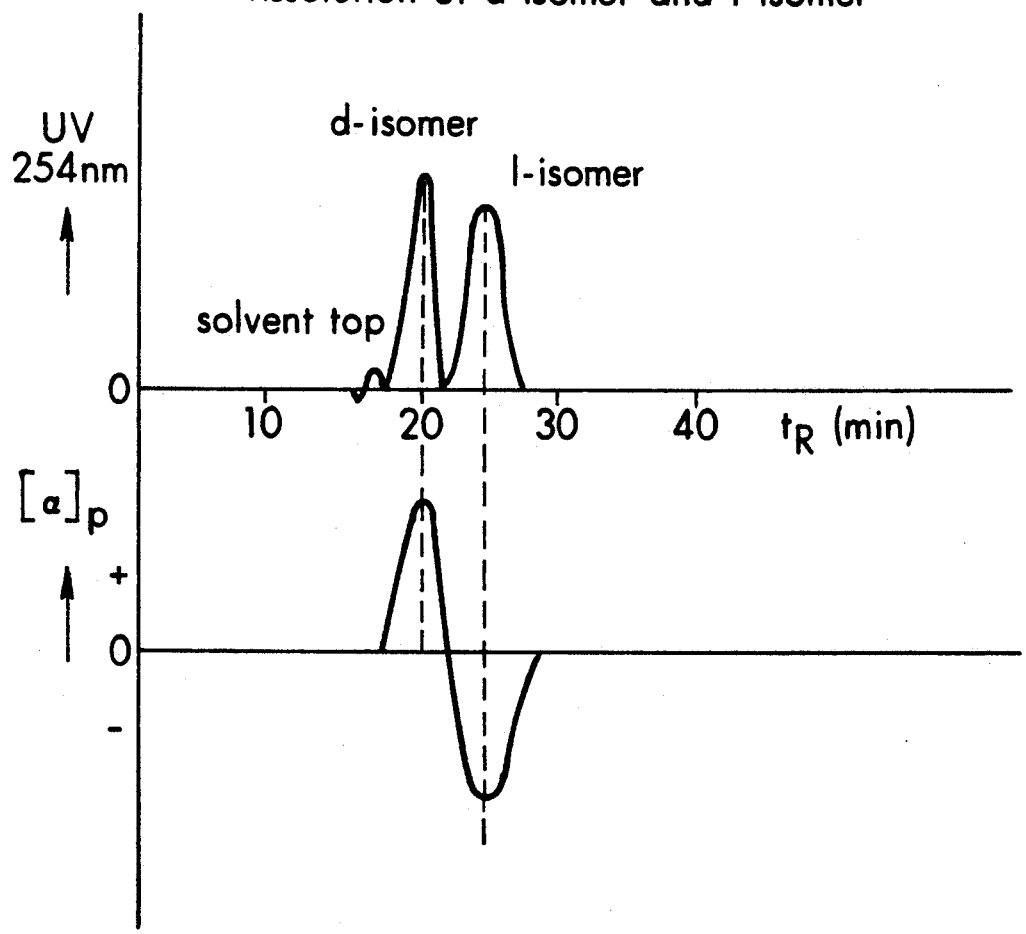

PROCESS OF OPTICALLY RESOLUTING OPTICALLY ACTIVE PLATINUM COMPLEX COMPOUND

BACKGROUND OF THE INVENTION

The present invention is a process of optically resoluting one optical isomer from the mixture of a platinum complex compound consisting of dextrorotatory and levorotatory optical isomers.

A platinum complex compound of Formula (1) is known as raw material of a carcinostatic agent, and the compound of Formula (1) is obtained by reacting potassium haloplatinate [$K_2Pt(II)X_4$] (X is chlorine, bromine or iodine) and 1,2-cyclohaxanediamine to produce a compound of Formula (2), to an aqueous solution of which is added two equivalences of a silver nitrate solution to precipitate and filter off the chlorine, the bromine or the iodine in the Formula (2) as silver chloride, silver bromide or silver iodide, respectively, and adding to the filtrate thereof an organic dibasic acid for cyclization.

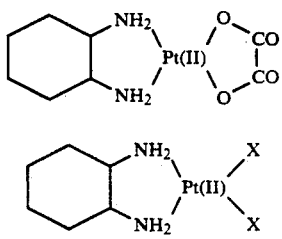

However, the compound of Formula (1) produced by this process is generally the mixture of a dextrorotatory substance (d-isomer) and a levorotatory substance (l-isomer). Generally, however, only one of the dextrorotatory substance and the levorotatory substance of the platinum complex compound is effective as a carcinostatic agent or the like. While, for example, only the dextrorotatory substance of the platinum compound of Formula (1) possesses the function as a carcinostatic agent, the levorotatory substance possesses toxicity to the contrary.

Even if a dextrorotatory dihalogen complex compound of Formula (2) is employed as starting material in order to obtain only the dextrorotatory compound of Formula (2), the retention of the optical isomerism is not guaranteed so that an optical isomer of 100% purity cannot be obtained in most cases. It is desirable, however, to optically resolute the dextrorotatory substance and the levorotatory substance at nearly 100% efficiency when high optical purity is required in such a case of the raw material of a carcinostatic agent.

Further, a process of accurately determining the optical purity of a platinum compound produced has not existed. The purity of the conventional mixture of a dextrorotatory substance and a levorotatory substance has only been indirectly estimated by means of its angle of rotation or circular duchroism. The industrial value of the compound of Formula (1) as the raw material of a carcinostatic agent remarkably increases if the purity of a desired platinum complex compound is exactly calculated.

SUMMARY OF THE INVENTION

An object of the invention is, in the light of the above problems of the prior art, to provide a process of optically resoluting an optically active platinum complex compound.

Another object of the invention is to provide a process of optically resoluting an optically active platinum complex compound into a dextrorotatory substance and a levorotatory substance one of which may be useful as raw material of a pharmaceutically active agent.

The present invention is a process of optically resoluting an optically active platinum complex compound which comprises optically resoluting a d-isomer and an l-isomer of a cis-Pt(II) complex of a 1,2-cyclohexanediamine isomer of Formula (3) characterized in that the mixture of the d-isomer and the l-isomer is optically resoluted by means of high performance liquid chromatography employing a column packed with a chiral filler.

According to the present invention, the optical resolution of a platinum complex compound essentially consisting of the mixture of a dextrorotatory substance and a levorotatory substance which cannot be resoluted in accordance with a normal resolution method due to the small structural difference can be easily performed utilizing the characteristics of a chiral filler. It is especially useful in case of the platinum complex compound of Formula (1) which may be employed as raw material of a carcinostatic agent because a pure reagent consisting of only one of the two optical rotation isomers having the pharmaceutical activities can be obtained.

Also in the resolution in accordance with the HPLC method of the present invention, the amount of impurities contaminated may be accurately determined by comparing peak heights of the two optical rotation isomers appearing on a chromatogram of a high performance liquid chromatography so that the determination of the optical purity may be simultaneously conducted.

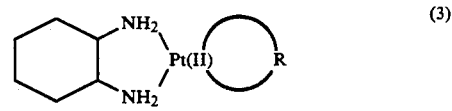

The chiral filler which may be employed in the present invention includes a cellulose ester derivative, a cellulose carbamate derivative, an amylose carbamate derivative, a polymethacryl acid ester, $\beta$- and $\gamma$-cyclodextrin, a polymethacrylamide derivative, an acidic glycoprotein, L-proline, hydroxyproline, L-valine, a filler prepared by adsorbing or binding (1R,2S)-2-carboxymetylamino-1,2- diphenylethanol to silica gel, a filler prepared by coordinating a metal ion to one of the said fillers, a filler prepared by adsorbing or binding a protein to aminated silica gel, a filler packed with a crown ether, a urea derivative kiral to silica gel treated with (3-aminopropyl)triethoxysilano, N(3,5-dinitrobenzoyl)-(R)-phenylglycine, DNR-L-leucine, (S)-1-($\alpha$-naphtyl) ethylamine and a filler bonding to (S)-2-(4-chlorophenyl) isovaleric acid. Depending on the kind of the platinum complex compound to be optically resoluted, one kind of those filler or two or more kinds thereof may be employed.

BRIEF DESCRIPTION OF THE DRAWINGS

FIG. 1 is a chromatogram obtained in the optical resolution of Example 1 wherein the upper portion thereof shows an amount of elution as a relative absorption amount of ultraviolet ray at 254 nm, and the lower portion thereof shows an amount of elution as a relative degree of rotation.

DETAILED DESCRIPTION OF THE INVENTION

The process of this invention is based on the inventors' knowledge of quantitatively resoluting the mixture of a dextrorotatory substance and a levorotatory substance by means of high performance liquid chromatography employing a column packed with a chiral filler.

A platinum complex compound which can be optically resoluted in accordance with the present invention is a compound designated by Formula (3) wherein R in Formula (3) is appropriately selected from Formulae (4), (5), (6), (7), (8) and (9). The compound of Formula (3) includes two kinds of optical isomers which differ from each other by a bonding direction of two amino groups of the four ligands coordinating a platinum metal which is a central metal of the complex compound, that is, a dextrorotatory substance and a levorotatory substance. The structural difference between the two optical isomers is so small that they cannot be optically resoluted in accordance with a conventional resolution method.

The present inventors have noticed an HPLC method employing an optically active chiral filler which may be employed for conducting the resolution of optical isomers utilizing the small structural difference. Upon investigation of various kinds of fillers, the inventors have found that the optical resolution of the platinum complex compound which is the mixture of a dextrorotatory substance and a levorotatory substance can be carried out by many chiral fillers.

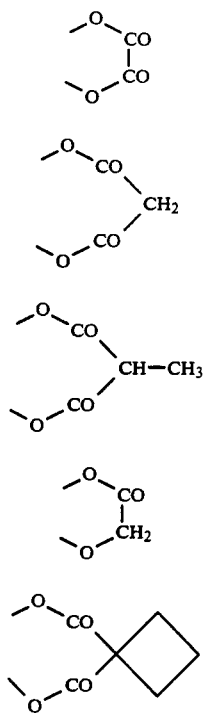

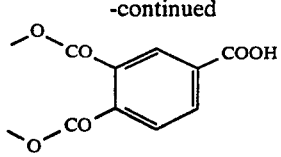

These chiral fillers include a cellulose ester derivative, a cellulose carbamate derivative, an amylose carbamate derivative, a polymethacryl acid ester, β- and γ-cyclodextrin, a polymethacrylamide derivative, an acidic glycoprotein, L-proline, hydroxyproline, L-valine, a filler prepared by adsorbing or binding (1R,2S)-2-carboxymetylamino-1,2-diphenylethanol to silica gel, a filler prepared by coordinating a metal ion to one of the said fillers, a filler prepared by adsorbing or binding a protein to aminated silica gel, a filler packed with a crown ether, a urea derivative chiral to silica gel treated with (3-aminopropyl)triethoxysilane, N(3,5-dinitrobenzoyl)-(R)-phenylglycine, DNB-L-leucine, (S)-1-(α-naphtyl)-ethylamine and a filler bonding to (S)-2-(4-chlorophenyl) isovaleric acid. Depending on the kind of the platinum complex compound to be optically resoluted, one kind of these filler or two or more kinds thereof may be employed.

While according to the HPLC method employing these fillers whether the complete resolution of the mixture into the dextrorotatory substance and the levorotatory substance may be taken place or only the incomplete resolution may be taken place can be confirmed, the amounts of impurities contaminated can be accurately determined by comparing peak areas of the two optically active substances appearing on the chromatogram. Since this peak area comparison method may utilize ultraviolet ray for detection, its sensitivity is better than the conventional method employing an angle of rotation or circular duchroism.

EXAMPLES

Although one example of a process of preparing a platinum complex compound which is the mixture of optical isomers and Examples of the optical resolution of the said optical isomers in accordance with the process of this invention, these Examples do not restrict the scope of the present invention.

EXAMPLE 1

After 56.25 g of potassium tetrachloroplatinate and 15.48 g of trans-dl-1,2-cyclohexanediamine were dissolved in water and mixed to proceed a reaction for three hours under agitation, the solution was filtered to obtain yellow needles of cis-dichloro(trans-dl-1,2-cyclohexanediamine) Pt(II). After this compound was suspended in 0.57 liter of water and a solution prepared by adding 38.04 g of silver nitrate to 0.28 liter of water was added thereto followed by agitation for three days at room temperature in the dark, the precipitate of silver nitrate was filtered off and removed. The deionization of such an ion as a silver ion, a nitrate ion, a halogen ion and a potassium ion dissolved in the filtrate was performed by passing the filtrate through a reverse osmosis membrane (Milipore K.K., NF 40, molecular weight to be divided: 400) at a pressure of 30 kgf/cm$^2$.

After active carbon was added to the solution for decolorization, the active carbon was completely removed by filtration. Addition of 14.63 g of oxalic acid to the filtrate and agitation for three hours produced a crude crystal of cis-oxalato(trans-dl-1,2-cyclohexanodiamine) Pt(II) at a yield of 80%.

Then, the desired cis-oxalato(trans-1-1,2-cyclohexanediamine) Pt(II) $(=(+)_{589}$-cis-$[Pt(OX)(R,R\text{-dach})])$ (hereinafter also referred to as "d-isomer") was resoluted from the cis-oxalato(trans-d-1,2-cyclohexanediamine) Pt(II) $(=(-)_{589}$-cis-$[Pt(OX)(S,S\text{-dach})])$ (hereinafter also referred to as "l-isomer") employing a solution prepared by dissolving 22.4 mg of the above crude crystal into 50 ml of methanol as a sample and employing high performance liquid chromatography (HPLC method) under the following conditions, and further the optical purity was determined.

Column: Glass-column having a height of 25 cm and an inner diameter of 4.6 mm packed with OC (Daicel Chemical Industries, Ltd., a filler prepared by adsorbing a cellulose carbamate derivative to silica gel)
Mobile phase: ethanol/methanol=30:70 (volume ratio)
Flow rate: 0.2 ml/min.
Column temperature: 40° C.
Detection:
    ultraviolet ray 254 nm
    optical rotation 589 nm The chromatogram of the optical resolution carried out under the said conditions is shown in FIG. 1. The upper portion of FIG. 1 shows an amount of elution as a relative absorption amount of ultraviolet ray at 254 nm, and the lower portion of FIG. 1 shows an amount of elution as a relative degree of rotation. The optical purity of the $(+)_{589}$-cis-$[Pt(OX)(R,R\text{-dach})]$ obtained was 100% $((-)_{589}$-cis-$[Pt(OX)(S,S\text{-dach})]$ was below 0.05%).

The optical purity was determined by means of an internal standard method employing the standard $(+)_{589}$-cis-$[Pt(OX)(R,R\text{-dach})]$ of the HPLC method as an internal standard.

At first, a calibration curve was prepared by plotting the ratios of component amounts of the standard l-isomer and the standard d-isomer to the ratios of the peak heights of the standard $(-)_{589}$-cis-$[Pt(OX)(S,S\text{-dach})]$ and the standard $(+)_{589}$-cis-$[Pt(OX)(R,R\text{-dach})]$. Then, the amounts of the d-isomers of Examples and Comparative Examples were measured by means of the HPLC method under the same conditions, and from the peak ratio obtained, the amounts of the examined components were determined and the content rates of the l-isomer in the sample were calculated.

Then, the optical purity was calculated as e.e. (excess rate of an enantiomer) in accordance with the following equation employing the content rates of the l-isomer calculated.

Optical Purity (%) = e.e. (%) = [{(content rate of d-isomer) − (content rate of l-isomer)}/{(content rate of d-isomer) + (content rate of l-isomer)}] × 100

The maximum relative standard deviation (RSD) in this case was about 0.1%, and the correlation coefficient of the linearity of the calibration curve was 0.9995628 showing the excellent linearity.

COMPARATIVE EXAMPLE 1

The crude crystal of the cis-oxalato(trans-1-1,2-cyclohexanediamine) Pt(II) was obtained in accordance with the same procedures of Example 1 except that in place of the trans-1-1,2-cyclohexanediamine of Example 1 which had not been optically resoluted, three kinds of trans-1-1,2-cyclohexanediamine which had been already optically resoluted and made by Aldrich, Tokyo Kasei K.K. and Wako Junyaku K.K. were employed.

Without the treatment by the chromatography method, the respective optical purities of the three crude crystals were measured to be 98.5%. This shows that the platinum complex compound obtained was the mixture of the two optically active substances even if the optically active compound was employed as starting material.

EXAMPLE 2

The platinum complex compound of Formula (10) was prepared in accordance with the same procedures of Example 1 except that trimellitic acid (1,3,4-tribenzene carboxylic acid) was employed in place of the oxalic acid (the compound was decomposed not less than 300° C.).

The optical purity of this platinum complex compound was determined in accordance with the same HPLC method of Example 1. The maximum relative standard deviation in this case was about 0.5%, and the correlation coefficient of the linearity of the calibration curve was 0.9993281 showing the excellent linearity.

EXAMPLE 3

The crude crystal of the cis-oxalato(trans-1-1,2-cyclohexanediamine) Pt(II) was obtained in accordance with the same procedures of Example 1 except that OJ (Daicel Chemical Industries, Ltd., a filler prepared by adsorbing a cellulose ester derivative to silica gel) was employed as a filler of column in place of OC.

The optical purity of this platinum complex compound was determined in accordance with the same HPLC method of Example 1. The maximum relative standard deviation in this case was about 1.0%, and the correlation coefficient of the linearity of the calibration curve was 0.9971753 showing the excellent linearity.

EXAMPLE 4

The crude crystal of the cis-oxalato(trans-1-1,2-cyclohexanediamine) Pt(II) was obtained in accordance with the same procedures of Example 1 except that AD (Daicel Chemical Industries, Ltd., a filler prepared by adsorbing an amylose carbamate derivative to silica gel) was employed as a filler of column in place of OC.

The optical purity of this platinum complex compound was determined in accordance with the same HPLC method of Example 1. The maximum relative standard deviation in this case was about 1.5%, and the correlation coefficient of the linearity of the calibration curve was 0.9965372 showing the excellent linearity.

EXAMPLE 5

The optical purity of an injection prepared by adding glucose to the cis-oxalato(trans-1-1,2-cyclohexanediamine) Pt(II) obtained in Example 1 was determined as follows.

At first, after 300 mg of this injection was suspended in 50 ml of methanol followed by two hours' stirring, the insoluble substances were removed by means of centrifugation for 30 minutes at 3000 rpm. Then, the filtration of the supernatant was conducted employing a membrane filter to provide a sample solution for HPLC. The conditions for HPLC were as follows.
Column: Stainless-column having a height of 25 cm and an inner diameter of 4.6 mm packed with OC (Daicel Chemical Industries, Ltd., a filler prepared by adsorbing a cellulose carbamate derivative to silica gel)
Mobile phase: ethanol/methanol = 30:70 (volume ratio)
Flow rate: 0.2 ml/min.
Column temperature: 40° C.
Detection: ultraviolet ray 254 nm The relative standard deviation in this case was 0.1%, the correlation coefficient of the linearity of the calibration curve was 0.9995628, and the optical purity of the injection was 100 e.e. expressed as an enantiomer excess rate.

Although the present invention has been described in conjunction with its preferred embodiments, it is readily understood that the invention is not limited by any of the details of the description and that various changes and modifications may be made by a person skilled in the art without departing from the spirit and scope of the present invention.

What is claimed is:

1. A process of optically resoluting an optically active platinum complex compound which comprises optically resoluting a d-isomer and an l-isomer of a cis-Pt(II) complex of a 1,2-cyclohexane-diamine isomer of Formula (3) [in this Formula, R designates one of Formulae (4), (5), (6), (7), (8) and (9)] characterized in that the mixture of the d-isomer and the l-isomer is optically resoluted by means of high performance liquid chromatography employing a column packed with a chiral filler (3)

(4)

(5)

(6)

(7)

(8)

(9)

2. A process as claimed in claim 1, wherein the chiral filler is one or more fillers selected the group consisting of a cellulose ester derivative, a cellulose carbamate derivative, an amylose carbamate derivative, a polymethacryl acid ester, β- and γ-cyclodextrin, a polymethacrylamide derivative, an acidic glycoprotein, L-proline, hydroxyproline, L-valine, a filler prepared by adsorbing or binding (1R,2S)-2-carboxymethylamino-1,2-diphenylethanol to silica gel, a filler prepared by coordinating a metal ion to one of the said fillers, a filler prepared by adsorbing or binding a protein to aminated silica gel, a filler packed with a crown ether, a urea derivative chiral to silica gel treated with (3-aminopropyl)triethoxysilane, N(3,5-dinitrobenzoyl)-(R)-phenylglycine, DNB-L-leucine, (S)-1-(α-naphtyl)ethylamine and a filler chemically bonding to (S)-2-(4-chlorophenyl)isovaloric acid.

* * * * *